United States Patent [19]

Boger et al.

[11] Patent Number: 4,518,565

[45] Date of Patent: May 21, 1985

[54] REAGENT TEST DEVICE HOLDER

[75] Inventors: David L. Boger, South Bend; Jerry T. Pugh; Jack Zuidema, both of Elkhart, all of Ind.

[73] Assignee: Miles Laboratories, Inc., Elkhart, Ind.

[21] Appl. No.: 501,609

[22] Filed: Jun. 6, 1983

[51] Int. Cl.³ .................... G01N 21/01; G01N 31/22; B01L 9/00
[52] U.S. Cl. ........................................ 422/58; 422/61; 422/104; 312/209; 435/805; 436/169
[58] Field of Search ........................ 422/55, 56, 61, 58, 422/102, 104; 312/209; 206/0.83, 0.84; 435/300, 805

[56] References Cited

U.S. PATENT DOCUMENTS 3,178,014 4/1965 Goldwasser ........................ 206/0.83
4,056,359 11/1977 Janin ........................................ 422/58

FOREIGN PATENT DOCUMENTS 1033714 6/1966 United Kingdom ............... 206/0.83
1535643 12/1978 United Kingdom ................. 422/55
2031583 4/1980 United Kingdom ................. 422/56

Primary Examiner—Barry S. Richman
Assistant Examiner—Joseph P. Carrier
Attorney, Agent, or Firm—Roger N. Coe

[57] ABSTRACT

Apparatus for accurately positioning and retaining multiple, individual reagent test devices in a holder. The holder consists of a base member and a top member in which the top member contains openings of at least the same number and dimension as the reagent pads appearing on the test devices. The holder permits the practical utilization of multiple, individual dip-and-read test devices in automated instrumentation.

6 Claims, 3 Drawing Figures

REAGENT TEST DEVICE HOLDER

BACKGROUND OF THE INVENTION

1. Field Of The Invention

The present invention relates to apparatus for accurately positioning and transporting multiple immunochemical, diagnostic or serological test devices and, more particularly, to such apparatus which facilitates automated processing of the test devices.

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so called "dip-and-read" type reagent test devices. Reagent test devices enjoy wide use in many analytical applications, especially in the chemical analysis of biological fluids, because of their relatively low cost, ease of usability, and speed in obtaining results. In medicine, for example, numerous physiological functions can be monitored merely by dipping a reagent test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constitutent is present. Such test devices provide the physician with a facile diagnostic tool as well as the ability to gage the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIASTIX, DEXTROSTIX, and others. Immunochemical, diagnostic or serological test devices such as these usually comprise one or more carrier matrices, such as absorbent paper, having incorporated therein a particular reagent or reactant system which manifests a detectable response, e.g., a color change in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constituent and/or its concentration in the sample. Some of these test devices and their reagent systems are set forth in U.S. Pat. Nos. 3,123,443; 3,212,855; 3,814,668; etc.

Regardless of whether the test device is used for the determination of biological fluid or the analysis of a commercial or industrial fluid, the normal procedure requires that each test device separately come in contact with the sample or specimen to be tested and then that the test device be visually or instrumentally analyzed. Means has been sought in the art for accurately positioning and retaining multiple individual test devices for automated processing. Prior to the present invention no known system had the capability of achieving the desiderata mentioned above in which multiple, individual test devices could be retained in apparatus for automatic processing without a change in format of the test device.

2. Description Of The Prior Art

The traditional dip-and-read test device can be manufactured at relatively low cost and it is convenient for an individual to use, but it is not well suited for use with highly automated equipment. For automated equipment to be of any advantage, it must result in a benefit with respect to cost, handling, and/or speed of obtaining information. Apparatus currently available for instrumentally reading individual reagent strips, such as the SERALYZER reflectance photometer or the CLINI-TEK reflectance photometer, manufactured and sold by the Ames Division of Miles Laboratories, Inc., Elkhart, Ind., requires that each reagent test device must be manually loaded into the instrument after contacting the test device with specimen or sample to be tested. Manual loading requires that the reagent test device be properly positioned in the instrument within a limited period of time after contacting the solution or substance to be tested. At the end of the analysis, each test device must be removed from the instrument for disposal.

A different format is presently used in the CLINI-LAB automated urinalysis system, which is manufactured and sold by the Ames Division of Miles Laboratores, Inc., Elkhart, Ind. The CLINILAB instrument uses a cassette containing reagent areas mounted seriatim on a continuous plastic substrate which is wound into a reel and housed in a cassette. While the CLINI-LAB reagent cassette is well suited for automation, the manufacturing cost for this type of format amounts to eight times that of the conventional dip-and-read test device format mentioned above.

In accordance with the present invention instrumental testing for immunochemical, diagnostic or serological purposes can be achieved using multiple conventional dip-and-read type reagent test devices. The apparatus results in an efficient, economical, rapid and convenient way of performing such analyses.

SUMMARY OF THE INVENTION

An object of the present invention is to provide a rigid holder for multiple reagent test devices.

Another object of the present invention is to provide a holder for multiple reagent test devices which permits the accurate positioning and transporting of such test devices in automated equipment.

Still another object of the present invention is to provide apparatus for conducting immunochemical, diagnostic or serological tests employing multiple, conventional, low cost, visual, dip-and-read reagent test devices.

In accordance with the present invention a holder for reagent test devices is provided having a base member and a top member which permit multiple individual reagent test devices to be accurately positioned parallel to one another, said top member having openings exposing each reagent area on the test devices for the application of specimen or sample to be tested and the taking of reflectance measurements.

BRIEF DESCRIPTION OF THE DRAWINGS

Other and further objects, advantages and features of the invention will be apparent to those skilled in the art from the following detailed description thereof, taken in conjunction with the accompanying drawings, in which.

DESCRIPTION OF THE PREFERRED EMBODIMENTS

The apparatus forming the subject matter of the present invention is characterized by a base member and top member which are or can be interconnected in such a manner to permit the insertion of multiple, individual reagent test devices into the apparatus such that the test devices are aligned parallel to each other. When the top member is closed reagent pads on the reagent test devices are exposed through openings in the top member corresponding to the location and dimension of the reagent pads on each test device. While the top member and base member are preferably permanently interconnected by hinge means in a fashion which permits the apparatus to be opened and closed, the base member and top member can, if desired, constitute separate members which become engaged in suitable fashion once multiple test devices have been placed onto or inserted into the base member.

Figure 1:
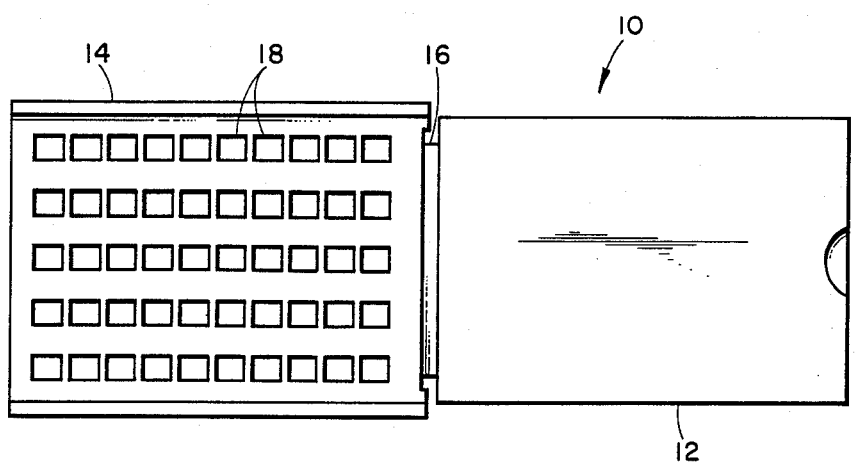
FIG. 1 is a top view of apparatus in accordance with the present invention, said apparatus being open to receive individual reagent test devices.

Turning now to FIG. 1 of the drawings, reagent test device holder 10 of the present invention is shown in an open position with base member 12 and top member 14 interconnected by means of flexible plastic interconnecting member 16. The design of the apparatus permits the entire assembly to be molded at one time. By having the top member permanently interconnected to base member 12 there is also the advantage that the top member cannot be misplaced or lost when the apparatus is opened.

Reagent test device holder 10 can be constructed of any suitable material such as polyethylene, polypropylene, ethylene copolymer, polystyrene, phenolic polymer, polycarbonate, acrylonitrile-butadiene-styrene copolymer, etc. Obviously, the material should be chosen to be durable, readily cleanable and relatively inexpensive. Aluminum or some other suitable metal could also be used for this purpose although metal holders tend to be somewhat more expensive than plastic holders. Another material which could be used, although less preferable, is cardboard which has been especially treated by a suitable coating to make it water impermeable.

Figure 2:
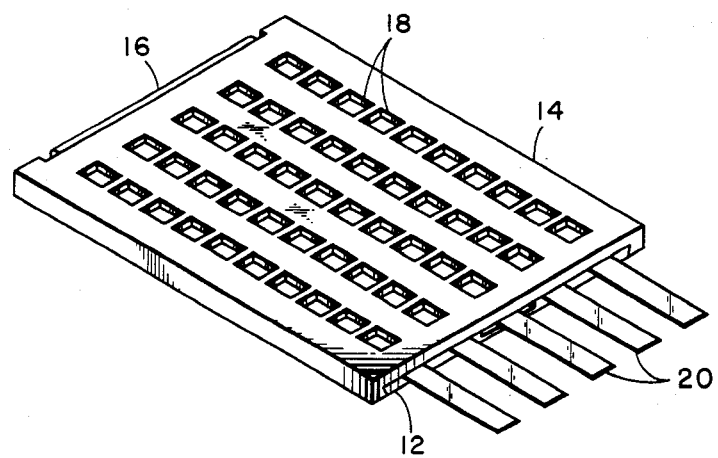
FIG. 2 is a perspective view of the apparatus of FIG. 1 in which multiple reagent test devices have been inserted, the top member being closed following the insertion of the test devices.

Base member 12 can have suitable ridges or other means which facilitate proper alignment of reagent test devices to assure that they become precisely parallel to one another. Top member 14, on the other hand, is constructed to have openings 18—18 which are of the same number and the same configuration as the reagent pads appearing on each reagent test device placed in base member 12. While the openings in the top member of the holder are preferably of the same configuration as the reagent pads on the reagent test device, these openings can be of any suitable configuration and, if desired, can be circular rather than square or rectangular. Top member 14 is designed to interconnect with base member 12 such that after multiple reagent test devices have been inserted into holder 10 the top member can be connected with the base member to achieve perfect registry between the openings 18—18 in top member 14 and the reagent pads on the reagent test devices 20—20, as shown in FIG. 2.

While the holders of the present invention can be made inexpensively such that the entire holder is disposable, the design of the holder apparatus facilitates the ready removal of used test devices and the reutilization of the reagent holder. Normally, all that is required in order to recondition a reagent holder device for reuse is simply removing any excess fluid by suitable blotting or through the use of controlled airflow. If desired, however, the reagent holders can be thoroughly cleaned after each use.

While the illustrated reagent holders are more or less rectangular in configuration, other suitable configurations can be used if desired. For example, circular holders could be employed with the reagent test devices radiating out from the center of the circular holder. The preferred rectangular configuration, however, permits the maximum number of reagent test devices to be inserted into a holder of the smallest possible dimensions.

As previously indicated, base member 12 and top member 14 can be interconnected by means 16. It will be understood, however, that any suitable means of permanently or temporarily interconnecting base member 12 and top member 14 can be used. For example, suitable hinges include a piano type hinge or any other suitable connecting hinge. Alternatively, base member 12 and top member 14 can be entirely separate, becoming interconnected when the two pieces are brought (snapped) together such that the members are aligned in a particular manner in registry with the reagent matrices of the test devices which have been inserted between the base member and the top member.

Figure 3:
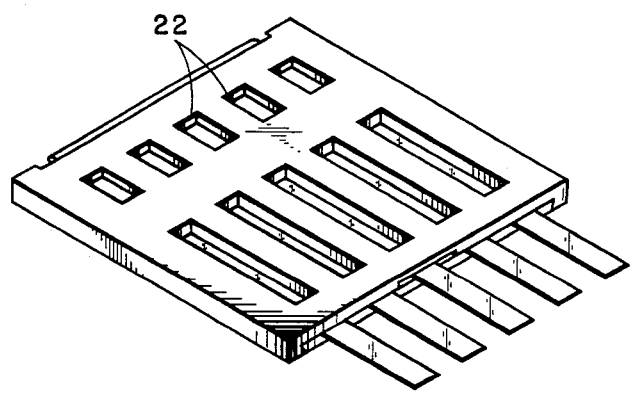
FIG. 3 is a perspective view of another embodiment of the invention designed to hold multiple, single pad reagent test devices.

While FIGS. 1 and 2 illustrate top member 14 containing ten openings 18—18 for each reagent test device, the number of openings can be varied depending upon a number of reagent pads present on the reagent test devices employed. In FIG. 3, for example, a holder for single pad reagent test devices is shown in which the top member of the holder contains a single opening 22—22 for each reagent test device.

Whereas FIGS. 2 and 3 illustrate the handle portion of the reagent test devices extending beyond the holder, it should be understood that the reagent holder can be made long enough to accommodate the entire reagent test device.

Once the reagent test devices have been inserted into the holder the reagent pads, which are exposed by the openings in the top member of the reagent holder, can be contacted with sample to be tested by any suitable means. For example, the entire holder can be dipped into the sample to be tested. Preferably, however, the sample to be tested is applied to the pads by convenient means such as placing one or more drops of the sample to be tested directly on each reagent pad. The latter procedure, obviously, can be automated using multiple dispenser tips interconnected to a common reservoir containing sample to be tested.

Because of the configuration of the holder apparatus, multiple test devices can be preloaded into each holder and individual or multiple holders fed into automated photometric apparatus for determining reflectance characteristics of treated reagent pads.

From the foregoing, it will be seen that this invention is well adapted to attain all of the ends and objects hereinabove set forth, together with other advantages which are obvious and which are inherent to the system. The apparatus of the present invention has the advantages of convenience, simplicity, relatively inexpensiveness, positiveness, effectiveness, durability, accuracy and directness of action. The invention substantially overcomes the problem of having to use different formats in order to facilitate inexpensive, rapid, immunochemical, diagnostic or serological testing. Conventional, low cost, visual type dip-and-read test devices can be used. There is no need to adopt a different or more expensive format. The holder apparatus of the present invention provides a very effective way of accurately positioning and transporting such test devices in automated instruments. Moreover, the openings in the top of the holder, through which the reagent pads are exposed, help prevent runover from occurring between adjacent reagent pads on the test devices. Runover can be a serious concern, particularly when incompatible reagents are present. Of course, the holder permits rapid and accurate alignment of all of the reagent pads in automated instruments upon alignment of the reagent holder.

Another advantage of the reagent holder is that the holder protects the reagent pads prior to use. This is a significant advantage in that occasionally one or more of the reagent pad areas on a reagent test device can become damaged during handling prior to or in the process of using the test device due to the fact that the reagent pad areas extend upward and are exposed on the surface of the test device substrate.

Another advantage of the reagent holder is that it facilitates contact of the reagent test devices with sample material and the presentation of the sample contacted test device to an instrument for performing a reflectance measurement thereby eliminating wasted test devices which sometimes occur with inexperienced users who have not developed a good technique for contacting specimen to be tested with the reagent test device.

Should there be a desire to store test devices for any period of time after testing, the holder of the present invention permits a convenient way of storing and retaining such test devices.

Obviously, many other modifications and variations of the invention as hereinbefore set forth can be made without departing from the spirit and scope thereof.

What is claimed is:

1. Apparatus for simultaneously making multiple analyses of liquid fluid, which apparatus comprises in combination:
    multiple, separate, dip-and-read reagent test devices, each consisting essentially of one carrier matrix pad, having reagent incorporated therein, attached to the upper surface of one end of an elongated, flexible substrate, wherein each said carrier matrix pad is raised to a height substantially above the surface of the substrate to which said matrix pad is attached; and
    reagent test device holding means for accurately positioning and retaining said carrier matrix pads of the reagent test devices immobile during analyses, said reagent test holding means consisting essentially of a base member for retaining said reagent test devices in parallel alignment, a separate top member containing openings substantially identical in size, number and configuration to the carrier matrix pads, hinge means for interconnecting the base member and the top member wherein the openings of said top member are in registry with each carrier matrix pad of said reagent test devices such that the reagent pads project into said openings so as to immobilize and isolate each carrier matrix pad during the analysis of a liquid fluid and substantially eliminate runover from occurring between adjacent carrier matrix pads on the reagent test devices, wherein said reagent test device holding means is constructed of a rigid, cleanable material of thickness such that the openings in said top member form wells into which liquid fluid to be analyzed is placed.

2. The apparatus of claim 1 in which the reagent test device holding means is plastic.

3. The apparatus of claim 1 in which the means for interconnecting the base member and top member of said reagent test holding means is a piano hinge.

4. Apparatus for simultaneously making multiple analyses of liquid fluid, which apparatus comprises in combination: multiple, separate, dip-and-read reagent test devices, each consisting essentially of a plurality of carrier matrix pads having reagent incorporated therein, attached to the upper surface of an elongated, flexible substrate in a horizontally spaced manner, wherein each said carrier matrix pad is raised to a height substantially above the surface of the substrate to which said matrix pad is attached; and reagent test device holding means for accurately positioning and retaining said carrier matrix pads of the reagent test devices immobile during analyses, said reagent test holding means consisting essentially of a base member for retaining said reagent test devices in parallel alignment, a separate top member containing openings substantially identical in size, number and configuration to the carrier matrix pads, hinge means for interconnecting the base member and the top member wherein the openings of said top member are in registry with each carrier matrix pad of said reagent test devices such that the reagent pads project into said openings so as to immobilize and isolate each carrier matrix pad during the analysis of a liquid fluid and substantially eleminate runover from occurring between adjacent carrier matrix pads on the reagent test devices, wherein said reagent test device holding means is constructed of a rigid, cleanable material of thickness such that the openings in said top member form wells into which liquid fluid to be analyzed is placed.

5. The apparatus of claim 4 in which the reagent test device holding means is plastic.

6. The apparatus of claim 4 in which the means for interconnecting the base member and top member of said reagent test holding means is a piano hinge.

* * * * *